United States Patent [19]

Schaar

[11] 4,212,296
[45] Jul. 15, 1980

[54] BANDAGE WITH PROTECTIVE MEMBER

[75] Inventor: Charles H. Schaar, Lake Zurich, Ill.

[73] Assignee: The Kendall Company, Boston, Mass.

[21] Appl. No.: 898,003

[22] Filed: Apr. 20, 1978

[51] Int. Cl.$^2$ ............................................. A61L 15/00
[52] U.S. Cl. ................................................... 128/156
[58] Field of Search ............... 128/112, 117, 120, 132, 128/149-151, 153-156

[56] References Cited

U.S. PATENT DOCUMENTS

| 432,798 | 7/1890 | Hirst | 128/132 R |
|---|---|---|---|
| 2,221,758 | 11/1940 | Elmquist | 128/154 |
| 2,367,690 | 1/1945 | Purdy | 128/132 R |
| 2,443,140 | 6/1948 | Larsen | 128/154 |
| 2,706,476 | 4/1955 | Diamond | 128/132 R |
| 2,785,677 | 3/1957 | Stumpf | 128/156 |
| 2,898,910 | 8/1959 | Gross et al. | 128/156 |
| 2,933,083 | 4/1960 | Kozdas | 128/89 |
| 3,062,210 | 11/1962 | Scholl | 128/156 |
| 3,063,448 | 11/1962 | Scholl | |
| 3,234,941 | 2/1966 | Tucker | 128/154 |
| 3,304,938 | 2/1967 | Perkins, Jr. | 128/132 R |
| 3,334,626 | 8/1967 | Schimmel | 128/155 |
| 3,782,377 | 1/1974 | Rychlik | 128/132 R |

Primary Examiner—C. Fred Rosenbaum
Attorney, Agent, or Firm—Powell L. Sprunger

[57] ABSTRACT

A bandage comprising, a pressure-sensitive tape strip having a central portion, and a pair of opposed end portions extending from the central portion for securing the bandage to a patient. The bandage has a protective member having a back surface secured to the front surface of the tape strip central portion, and a front surface defining a cavity. The bandage also has an absorbent pad received in the cavity with the protective member absorbing blows applied to the bandage to minimize trauma to a wound covered by the bandage.

6 Claims, 6 Drawing Figures

U.S. Patent         Jul. 15, 1980         4,212,296
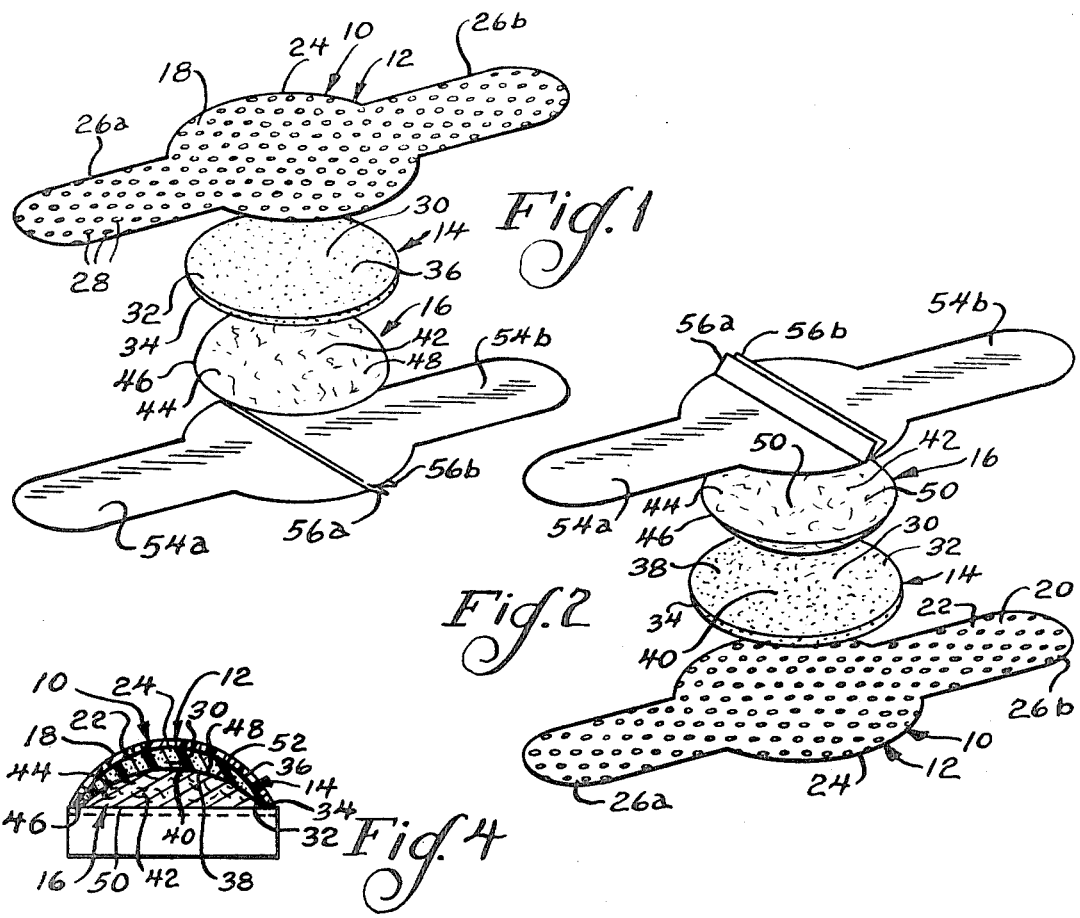
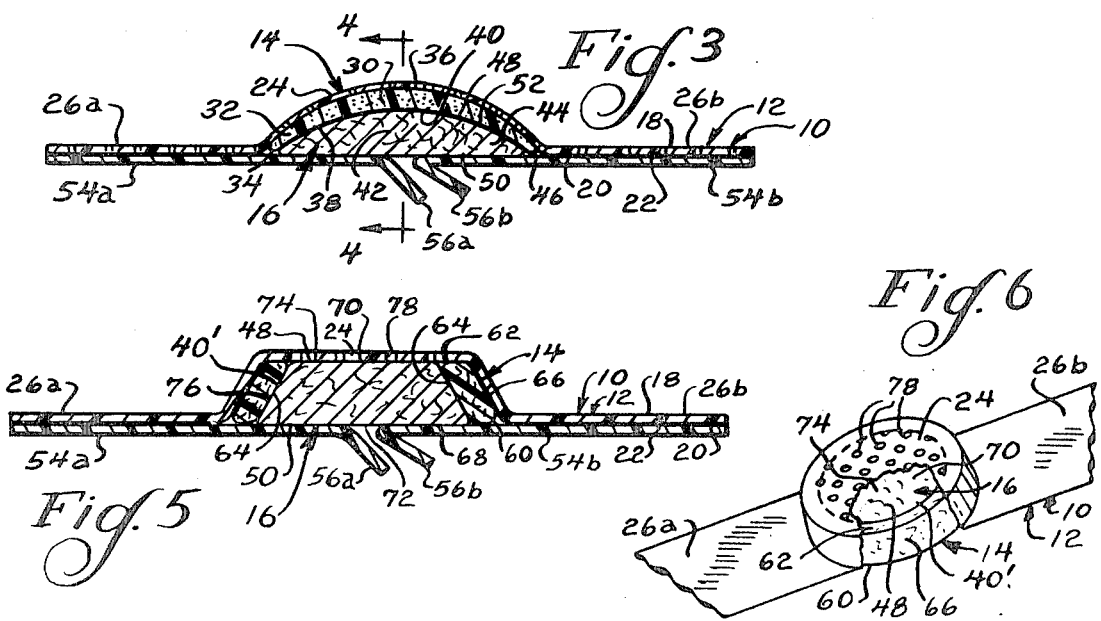

BANDAGE WITH PROTECTIVE MEMBER

BACKGROUND OF THE INVENTION

The present invention relates to absorbent articles, and more particularly to bandages.

A various assortment of bandages have been proposed for covering a wound on a patient during the healing process. Such bandages are normally constructed with a tape strip and an absorbent pad secured to the strip for placement over the wound. Although for many purposes such bandages have been found satisfactory, they do not afford sufficient protection for the wound in certain instances. When the site of the wound is located in an area of the body which is frequently subjected to shocks and blows during healing, the resulting forces are transmitted through the bandage to the wound causing continued agitation of the wound and prolonged healing.

SUMMARY OF THE INVENTION

A principal feature of the present invention is the provision of an improved bandage of simplified construction.

The bandage of the present invention comprises, a tape strip having a back surface, a front surface, adhesive on the front surface, a central portion, and a pair of opposed end portions extending from the central portion for securing the bandage to a patient. The bandage has a protective member of foam material having a central region of maximum thickness and an edge area tapering from the central region to an outer edge extending peripherally around the protective member. The protective member has a generally convex back surface secured to the front surface of the strip central portion with the protective member edge generally aligned with the front surface of the strip end portions, and the protective member has a generally concave front surface defining a cavity facing away from the strip central portion. The bandage has an absorbent pad having a central region of enlarged thickness and an edge area tapering from the pad central region toward an outer edge extending peripherally around the pad. The pad has a generally convex back surface secured to the front surface of the protective member with the pad received in and substantially filling the cavity, and with the outer edge of the pad being located adjacent the outer edge of the protective member. The pad also has a generally planar front surface generally aligned with the strip end portions.

A feature of the present invention is that the bandage may be readily secured to a patient utilizing the end portions of the tape strip.

Another feature of the invention is that the protective member substantially covers the back surface of the absorbent pad, and isolates the pad from the external environment during use of the bandage.

Thus, a feature of the present invention is that the protective member absorbs shocks and blows during use of the bandage.

Yet another feature of the invention is that the bandage may be applied to a region of the body which is frequently subjected to shocks and blows, such as the ends of the fingers or thumb, in order to minimize trauma to the wound and facilitate the healing process.

Further features will become more fully apparent in the following description of the embodiments of this invention and from the appended claims.

DESCRIPTION OF THE DRAWINGS

In the drawings:

FIG. 1 is an upper exploded perspective view of a bandage of the present invention;

FIG. 2 is a lower exploded perspective view of the bandage of FIG. 1;

FIG. 3 is a sectional view of the bandage of the present invention;

FIG. 4 is a sectional view taken substantially as indicated along the line 4—4 of FIG. 3;

FIG. 5 is a sectional view of another embodiment of the bandage of the present invention; and FIG. 6 is a fragmentary perspective view of the bandage of FIG. 5.

DESCRIPTION OF THE PREFERRED EMBODIMENTS

Referring now to FIGS. 1-4, there is shown a bandage generally designated 10 having a pressure-sensitive tape strip 12, a protective member 14, and an absorbent pad 16. The tape strip 12 has a back surface 18, a front surface 20, and adhesive 22 covering the front surface 20 of the tape strip 12. The tape strip 12 has a central portion 24, and a pair of opposed end portions 26a and 26b extending from the central portion 24 for securing the bandage to a patient during use. As shown, the central portion 24 may have arcuate edges defining a greater width of the central portion 24 relative the end portions 26a and b. The tape strip may be made from any suitable material, such as polyethylene, and the tape strip may be provided with a plurality of apertures 28 to permit breathability through the bandage. Any suitable adhesive may be utilized for the tape strip.

The protective member 14 has a central region 30 of enlarged thickness and an edge area 32 which tapers from the central region 30 to an outer edge 34 extending peripherally around the protective member 14. As shown, the protective member 14 has a generally convex back surface 36, and a generally concave front surface 38 defining a cavity 40. The back surface 36 of the protective member 14 is secured to the strip central portion 24 by the adhesive 22, with the outer edge 34 of the protective member 14 generally aligned with the front surface of the strip end portions 26a and b, and with the cavity 40 facing away from the strip central portion 24. The protective member 14 may be made of any suitable material which absorbs shocks and blows, such as a polyurethane foam. In a preferred form, the protective member is made from a relatively firm material, such as foamed polystyrene, in order to absorb relatively high impact forces.

The absorbent pad 16 has a central region 42 of enlarged thickness and an edge area 44 which tapers from the central region 42 toward an outer edge 46 extending peripherally around the pad 16. The pad has a generally convex back surface 48, and a generally planar front surface 50. The pad 16 is received in the protective member cavity 40, and the back surface 48 of the pad 16 is secured by adhesive 52 to the front surface 38 of the protective member 14. The pad 16 is of a size to substantially fill the protective member cavity 40, such that the outer edge 46 of the pad 16 is located adjacent the outer edge 34 of the protective member 14. In addition, the front surface 50 of the pad 16 is generally aligned with the front surface of the strip end portions 26a and b such that the bandage 10 defines a generally planar front surface for the patient during use. The pad 16 may be of any suitable type, such as a layer of absorbent material and a film with openings defining the front surface of the pad, as disclosed in U.S. Pat. No. 2,923,298.

The bandage 10 may have a pair of release sheets 54a and 54b, such as silicone coated paper, releasably attached to the adhesive 22 on the strip end portions 26a and b, with the release sheets 54a and b having associated folded end portions 56a and 56b. In use, the end portions 56a and b may be gripped by the user in order to remove the release sheets 54a and b from the tape strip 12 and expose the adhesive 22 on the strip end portions 26a and b for securing the bandage to the user.

The protective member 14 substantially covers the back surface 48 of the absorbent pad 16, such that the protective member 14 isolates the pad 16 from the external environment while the bandage is worn. Thus, the protective member 14 provides a shock absorbing medium intermediate the wound site beneath the pad and the outside of the bandage. In this manner, the protective member minimizes trauma to the wound during use of the bandage in order to facilitate the healing process. The bandage of the present invention may be conveniently used on areas of the body which are frequently subjected to bumps and blows, such as the ends of the fingers and thumb, thus isolating the wound site from the external environment and protecting the wound during use of the bandage.

Another embodiment of the present invention is illustrated in FIGS. 5 and 6, in which like reference numerals designate like parts. In this embodiment, the protective member 14 has a generally annular shape and defines a portion of the cavity 40'. The protective member 14 has a front edge 60, a back edge 62, an inner side surface 64 facing the cavity 40', and an outer side surface 66 facing the tape strip 12, with the protective member 14 defining a front opening 68 at the front edge 60, and a back opening 70 at the back edge 62. As shown, the walls of the protective member 14 are tapered inwardly from the front edge 60 toward the back edge 62. The pad 16 has a frustro-conical shape defining a front surface 72, a back surface 74, and a tapered side surface 76 extending between the front and back surfaces 72 and 74 of the pad. When received in the cavity 40', the front surface 72 of the pad 16 is generally aligned with the front edge 60 of the protective member, while the back surface 74 of the pad is generally aligned with the back edge 62 of the protective member. The tape strip 12 has a central portion 24 extending across the back opening 70 of the protective member and along opposed end portions of the protective member outer side surface 66. The central strip portion 24 may have a plurality of apertures 78 communicating with the cavity 40' to permit breathability of the pad 16 through the strip 12. As before, the protective member 14 absorbs blows during use of the bandage.

The foregoing detailed description is given for clearness of understanding only, and no unnecessary limitations should be understood therefrom, as modifications will be obvious to those skilled in the art.

I claim:

1. A bandage comprising:
   a tape strip having a back surface, a front surface, adhesive on said front surface, a central portion, and a pair of opposed end portions extending from said central portion for securing the bandage to a patient;
   a protective member of foam material having a central region of enlarged thickness and an edge area tapering from said central region to an outer edge extending peripherally around the protective member, said protective member having a generally convex back surface secured to the front surface of said strip central portion with said protective member edge generally aligned with the front surface of said strip end portions, and said protective member having a generally concave front surface defining a cavity facing away from said strip central portion; and
   an absorbent pad having a central region of enlarged thickness and an edge area tapering from the pad central region toward an outer edge extending peripherally around the pad, said pad having a generally convex back surface secured to the front surface of the protective member with said pad received in and substantially filling said cavity, said outer edge of the pad being located adjacent the outer edge of the protective member, and said pad having a generally planar front surface generally aligned with the front surface of said strip end portions.

2. The bandage of claim 1 wherein said tape strip central portion includes adhesive on said front surface to secure the protective member to the tape strip.

3. The bandage of claim 1 including adhesive intermediate the protective member and pad to secure the pad to the front surface of the protective member.

4. The bandage of claim 1 wherein said protective member is constructed from foamed polystyrene.

5. The bandage of claim 1 wherein the width of said strip central portion is greater than the width of said end portions.

6. The bandage of claim 1 including release sheet means releasably attached to the adhesive on said strip end portions.

* * * * *